United States Patent
Griffiths et al.

(10) Patent No.: US 10,722,294 B2
(45) Date of Patent: Jul. 28, 2020

(54) SURGICAL INSTRUMENT

(71) Applicant: ALESI SURGICAL LIMITED, Cardiff (GB)

(72) Inventors: Dominic Griffiths, Cardiff (GB); Nicholas Evans, Cardiff (GB); Peter Bannister, Cardiff (GB); Neil Warren, Cardiff (GB); Francis Kweku Egyin Amoah, Cardiff (GB)

(73) Assignee: ALESI SURGICAL LIMITED, Cardiff (GB)

( * ) Notice: Subject to any disclaimer, the term of this patent is extended or adjusted under 35 U.S.C. 154(b) by 341 days.

(21) Appl. No.: 15/432,207

(22) Filed: Feb. 14, 2017

(65) Prior Publication Data

US 2017/0151012 A1 Jun. 1, 2017

Related U.S. Application Data

(63) Continuation of application No. PCT/GB2015/052365, filed on Aug. 14, 2015.

(30) Foreign Application Priority Data

Aug. 15, 2014 (GB) .................................. 1414529.6

(51) Int. Cl.
*A61B 18/14* (2006.01)
*A61B 18/04* (2006.01)
(Continued)

(52) U.S. Cl.
CPC ........ *A61B 18/1445* (2013.01); *A61B 18/042* (2013.01); *A61B 18/1442* (2013.01);
(Continued)

(58) Field of Classification Search
CPC .......... A61B 18/042; A61B 2018/1213; A61B 2018/1273; A61B 2018/122; A61B 18/1442; A61B 18/1445; A61B 2018/00589; A61B 2018/00601; A61B 2018/1266; A61B 2018/1465
See application file for complete search history.

(56) References Cited

U.S. PATENT DOCUMENTS 6,063,084 A * 5/2000 Farin .................. A61B 18/1492
606/40
6,379,427 B1 4/2002 Siess
(Continued)

FOREIGN PATENT DOCUMENTS

GB 2492862 B 2/2014
WO 2013068724 A1 5/2013

*Primary Examiner* — Eun Hwa Kim
*Assistant Examiner* — Catherine Premraj
(74) *Attorney, Agent, or Firm* — Joseph C. Zucchero; Carolyn S. Elmore; Elmore Patent Law Group, P.C.

(57) ABSTRACT

A surgical instrument is disclosed which comprises a surgical device actuatable for performing a surgical procedure, the device having an electrically conductive portion, and an ion-generating electrode integrally arranged with respect to the surgical device, the ion-generating electrode having an ion emission zone. The ion emission zone of the ion-generating electrode and the electrically conductive portion of the surgical device are moveable relative to each-other between a first position and a second position.

18 Claims, 6 Drawing Sheets

(51) Int. Cl.
*A61B 18/00* (2006.01)
*A61B 18/12* (2006.01)

(52) U.S. Cl.
CPC ........... *A61B 2018/00589* (2013.01); *A61B 2018/00601* (2013.01); *A61B 2018/122* (2013.01); *A61B 2018/1266* (2013.01); *A61B 2018/1273* (2013.01); *A61B 2018/1465* (2013.01)

(56) References Cited

U.S. PATENT DOCUMENTS

| | | | | |
|---|---|---|---|---|
| 2007/0000501 | A1* | 1/2007 | Wert | A61B 18/1206 128/898 |
| 2008/0071264 | A1* | 3/2008 | Azure | A61B 18/1477 606/41 |
| 2008/0161796 | A1* | 7/2008 | Cao | A61B 18/1492 606/41 |
| 2009/0299362 | A1* | 12/2009 | Long | A61B 18/1492 606/34 |
| 2012/0067212 | A1* | 3/2012 | Warren | A61B 18/00 95/57 |
| 2012/0150172 | A1* | 6/2012 | Ortiz | A61B 18/1477 606/41 |
| 2014/0031813 | A1* | 1/2014 | Tellio | A61B 90/11 606/34 |

* cited by examiner

SURGICAL INSTRUMENT

This invention relates to surgical instrument, in particular an integrated surgical instrument capable of causing removal or reduction of smoke during laparoscopic or other intracorporeal procedures or open surgery.

In this specification, the words particles, smoke, smoke particles, and related terms are intended to encompass any particles, or molecules or matter suspended in an atmosphere included suspended droplets formed by heat or cold.

During surgery, target tissues can be conveniently dissected and coagulated using energised instrumentation, such as laser, ultrasonic or electrosurgical surgical devices. An unwanted side effect of many such powered instruments is the production of smoke. In intracorporeal "minimally invasive procedures" this is exacerbated by the preferably low rate of replacement of the carbon dioxide insufflation gas that is used to create a working environment for the surgical procedure. As such, the smoke accumulates to a greater extent than during open surgical procedures, where it dissipates into the surgical operating room. This accumulation of the smoke hinders the surgeon's view of the site to be operated or observed. The poor view can be hazardous to the patient when surgical procedures are being performed and as such it is desirable to remove the smoke and to improve the surgeons' visibility. Furthermore, for those in the operating room the continual "chronic" exposure to surgical smoke may be deleterious to health. One method of removing the smoke is to apply a vacuum tube that removes the smoke particles from the localised region to an external collecting device. Alternatively, it is possible to remove smoke particles suspended in local atmosphere using ionised particles as described in the applicants own International patent application. This can be achieved by using a separate ion generator i.e. separate ion-generating electrode and powered surgical device as shown in FIG. 1 or an integrated ion generator i.e. ion-generating electrode and surgical device combined, as shown in FIGS. 2 and 3. Both of these instrument configurations have challenges associated with them. In the former arrangement surgeons can encounter unwanted interactions between the ion generator and the surgical device. For example, an accidental brushing or positioning of the discrete ion generator and an electrically uninsulated surgical device in a close proximity (<10 mm) with each other results in an accumulation of electrostatic charge on the surgical device. These charges can be dissipated when the surgeon makes contact with other objects, for example the patient or the surgical trolley which is near to ground voltage potential. Whilst the electrostatic discharges are benign in intensity there is a risk of involuntary movement of the patient (depending on sedation) and/or the surgeon, and as such this provides a potential detrimental effect to the accuracy of the surgery. To minimise this effect, the surgical team must manually adjust the distances between the ion generator i.e. ion-generating electrode and the surgical device which can be an inconvenience and often impractical. Another problem associated with this arrangement is that the team may wish to select when to enable and disable the ion generator manually.

In the latter integrated arrangement, the surgical instrument has been found to obstruct the distribution of ions and the resulting effect of the smoke removal is hindered. Further, the distance between the ion generator and the surgical instrument is fixed so any undesired electrostatic charge dissipation cannot be accommodated for. While it is efficacious to place the ion-generating electrode near the distal end of the powered surgical instrument, there is also an imperative to avoid placing the ion-generating electrode such that the line of sight between the distal end of the powered surgical instrument and the objective lens of a laparoscopic telescope is significantly obscured.

Therefore, the present invention and its embodiments are intended to address at least some of the above described problems and desires. In particular, to optimise the smoke clearing performance of the device, with the benefit of reducing the likelihood of accidental accumulation of charge in the surgical accessories in a reliable and reproducable way.

According to a first aspect of the invention there is provided a surgical instrument comprising:

a surgical device actuatable for performing a surgical procedure, the device having an electrically conductive portion, and an ion-generating electrode integrally arranged with respect to the surgical device, the ion-generating electrode having an ion emission zone, wherein the ion emission zone of the ion-generating electrode and the electrically conductive portion of the surgical device are moveable relative to each-other between a first position and a second position.

The relative movement of the ion-generating electrode and the conductive portion enables the minimisation of arbitrary electrical pathways between the RF outputs and surroundings thereby reducing the risk of RF burn or interference with contact quality circuits.

In the first position the distance between the ion generation zone of the ion-generating electrode and the conductive portion of the surgical device may be of a value that lies outside of a pre-determined range and in the second position/configuration, the distance between the ion generation zone of the ion-generating electrode and the conductive portion of the surgical device may be of a value that lies within a pre-determined range. The pre-determined range may be substantially 10-50 mm. The first position may be a stored position so as to minimise the obstructive effect of the ion-generating electrode.

The surgical instrument may further comprise a proximity detector for sensing the relative separation between the ion emission zone and the conductive portion of the surgical device in the first and second position. The proximity detection is ultimately provided by the high voltage source.

There may be included multiple ion emission zones on the ion-generating electrode which are selectively moveable dependent upon the sensed separation between the ion emission zones and the conductive portion of the surgical device. This enables ion emission from a selection of ion emission zones that are not subject to proximity constraints, and prevents use of ion emission zones that lies outside of a predetermined range.

The surgical instrument may further comprise an actuator for actuating the surgical device for performing the surgical procedure, wherein the actuation is manually triggered by the surgeon.

The actuator may be further arranged to enable the relative movement between the first and second positions. Therefore, a pre-determined default position is applied once the activator has been triggered by the surgeon.

The actuator may be further arranged to actuate the emission of ions from the ion emission zone of the ion-generating electrode when the ion emission zone of the ion-generating electrode is in the second position.

The actuation of the emission of ions from the ion emission zone of the ion-generating electrode may be prohibited when the ion emission zone of the ion-generating electrode is in the first position. This ensures that ion emission is only generated when the ion emission zone is positioned within the predetermined range (the second position) and so minimises exposure if the patient to ion current. This follows the principle that it is undesirable to apply any more energy to the patient that is absolutely needed for the intended surgical benefit, but may also minimise nuisance proximity alarm indications when smoke clearing is not required.

The second position may be dependent upon the proximity of patient tissue or other conductive surface with respect to the ion emission zone of the ion-generating electrode. Any conducting surface is considered by the device, therefore whilst the vicinity of the conductive portion of the surgical device is of importance, so to is the location of tissue of the patient.

The surgical device may comprise an elongate portion and the ion emission zone of the ion-generating electrode may be moveable relative to the elongate portion.

The ion emission zone may be moveable between the first position and the second position along an arcuate path.

The ion emission zone may be formed of a sharpened or fibrous element. This increases the surface area of ion emission and improves the uniformity of the emission.

The sharpened or fibrous element may terminate an electrically conducting arm portion.

A portion of the arm may be flexible. This enables the arcoidal path of the ion emission zone to be realised.

The arm may be formed of memory metal. This has the desirable property of being conductive, flexible and positionable between a first and second position, whereby the first and second position may be sustained as desired.

A portion of the arm may be attached to an outer surface of the surgical device.

A resistive load may be electrically coupled to an end of the conductor. This renders more benign any discharges to the surgical device.

The resistive value of the resistive load may be in a range of 1 to 100 M Ohms.

At least part of the ion-generating electrode may be formed of a resistive material having an effective resistance in the range of 1 to 100 M Ohms.

In a second aspect of the invention there is provided a surgical instrument assembly for removing particles suspended in a patient, the assembly comprising the surgical instrument according to the first aspect and a DC voltage electrical source, the ion-generating electrode of the surgical instrument being electrically couplable with a pole of the electrical source and the patient being electrically couplable with the other pole of the electrical source.

In a third aspect of the invention there is provided a method of reducing or removing particles suspended in a local atmosphere, during and/or after surgical procedures, comprising use of the above-mentioned surgical instrument assembly, the method comprising the steps in any suitable order, of:
  a) moving the ion emission zone of the ion-generating electrode which is integrally related to the surgical device from a first position to a second position with respect to the electrically conductive portion of the surgical device;
  b) commencing emission of ions from the ion emission zone to thereby ionise said particles in the localised atmosphere and attract said particles towards the patient.

On actuation of the surgical device the ion-generating electrode may be automatically moved from the first position to the second position. Actuation is commenced by the surgeon.

On actuation of the surgical device by the actuator, the ion emission zone of the ion-generating electrode may be activated.

The actuator may be arranged to cause actuation of the surgical device, the deployment of the ion emission zone of the ion-generating electrode from a first position to the second position and the generation of the ions from the ion emission zone.

The generation of ions may be actuated subsequent to moving the ion emission zone of the ion-generating electrode from the first position to the second position.

The surgical device may be actuatable for performing a surgical procedure, the device having an electrically conductive portion,
at least a portion of the ion-generating electrode being integrally arranged with respect to the surgical device and comprising an ion emission zone,
wherein the ion emission zone of the ion-generating electrode and the electrically conductive portion of the surgical device are moveable relative to each other between a first position and a second position.

Multiple ion emission zones on the ion-generating electrode may be selectively deployed in dependence upon the detected proximity of surrounding conducting surfaces.

Whilst the invention has been described above it extends to any inventive combination of the features set out above, or in the following description, drawings or claims. For example, any features described in relation to any one aspect of the invention is understood to be disclosed also in relation to any other aspect of the invention.

The invention will now be described, by way of example only, with reference to the accompanying drawings, in which.

Figure 1:
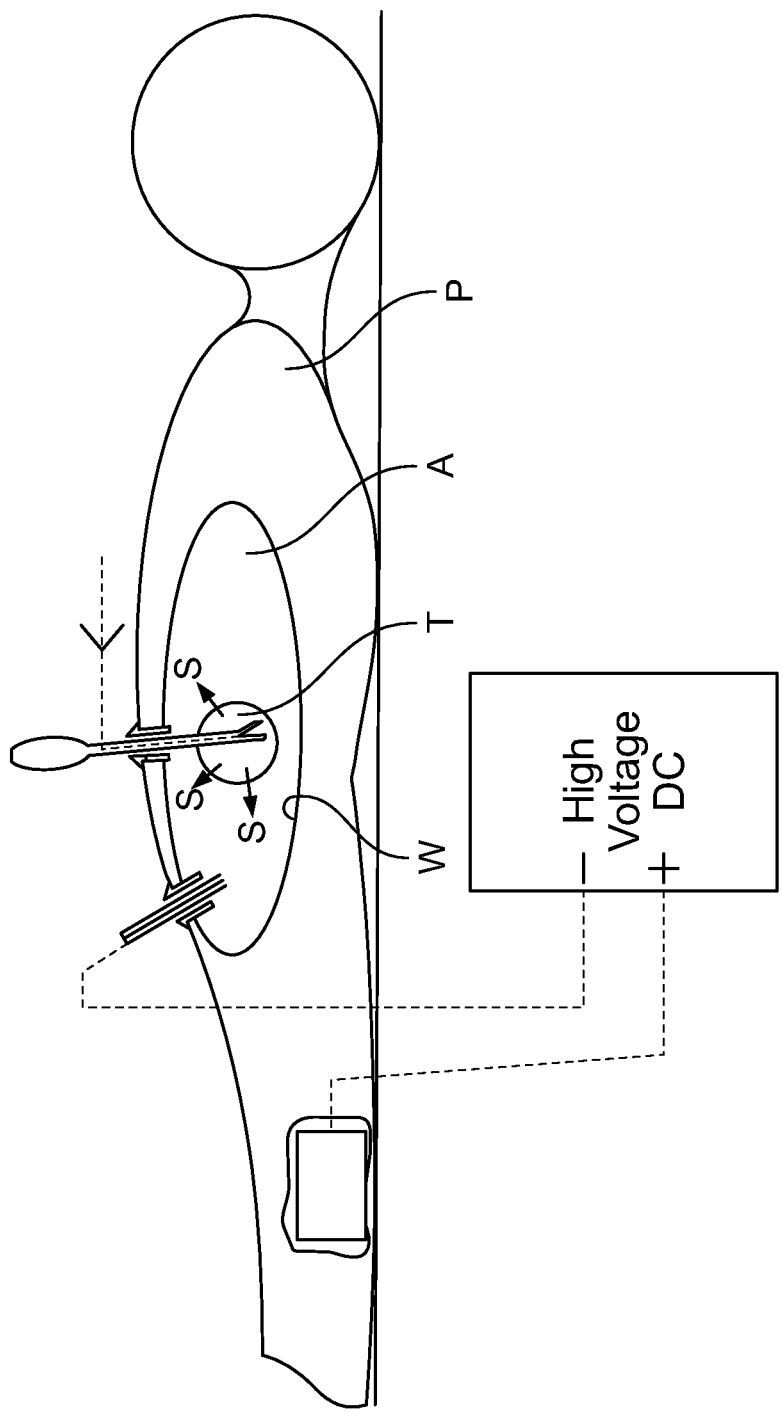
FIG. 1 is a discrete ion generator and surgical instrument of the prior art in use on a patient.
Figure 2:
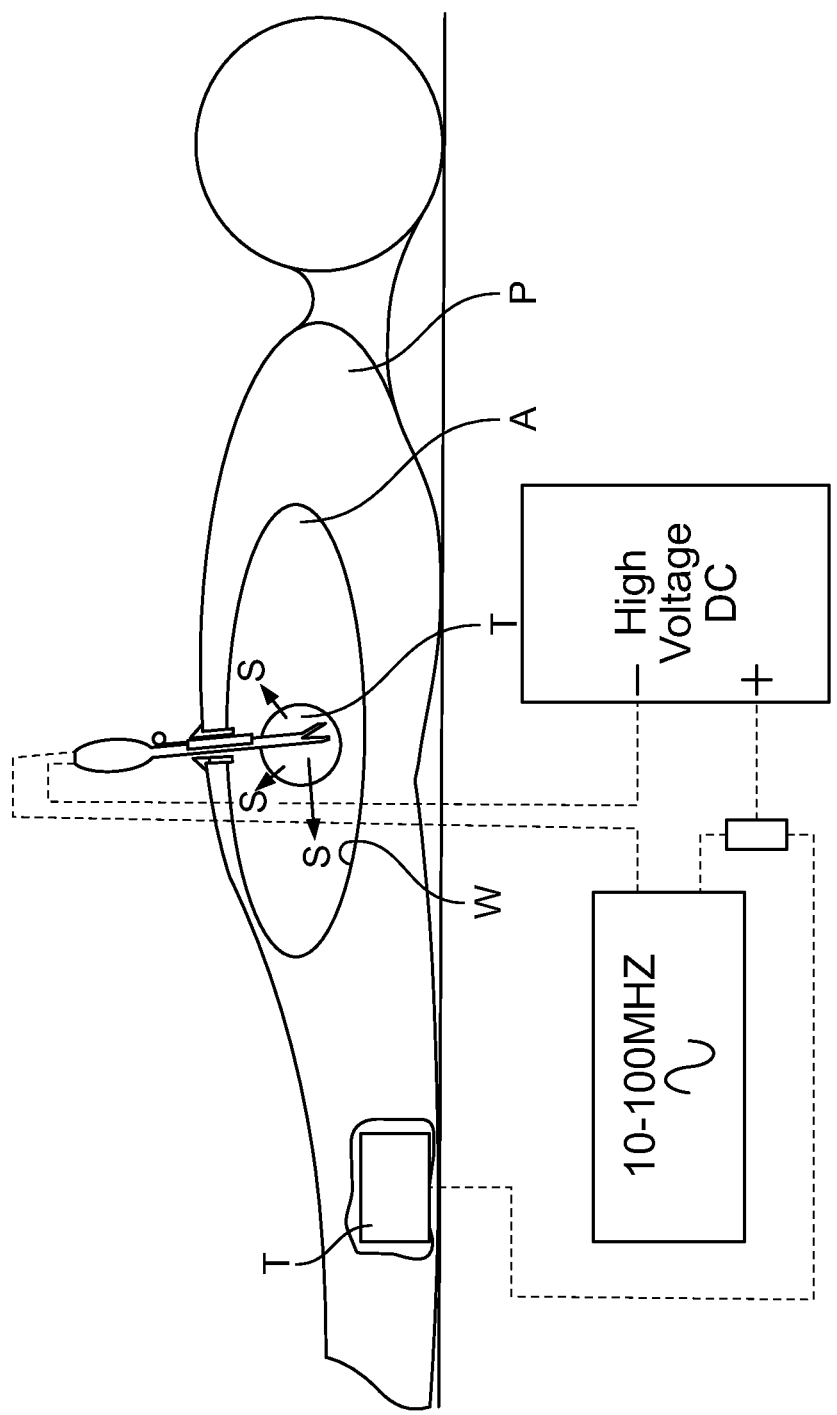
FIG. 2 is an integrated ion generator and surgical instrument of the prior art in use on a patient.
Figure 3:
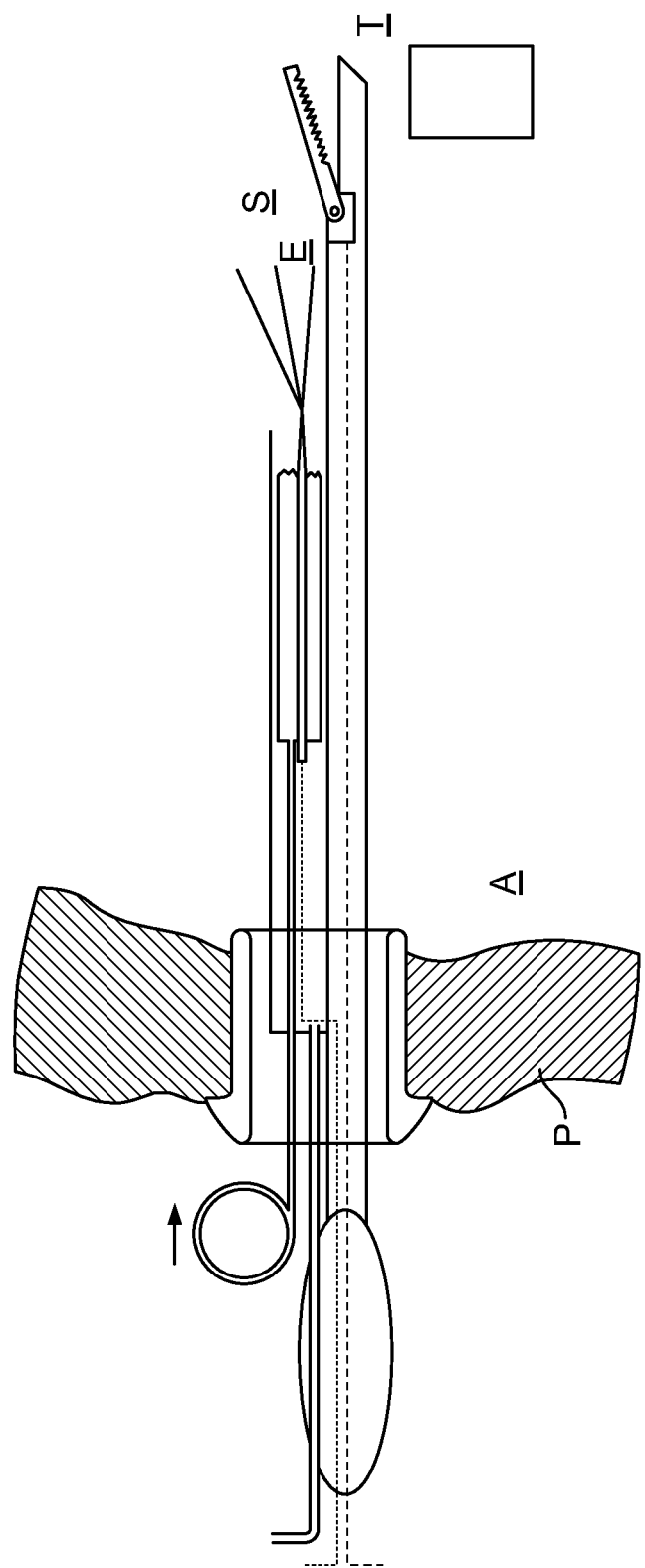
FIG. 3 is a schematic view of the integrated ion generator and surgical instrument of the prior art.
Figure 4:
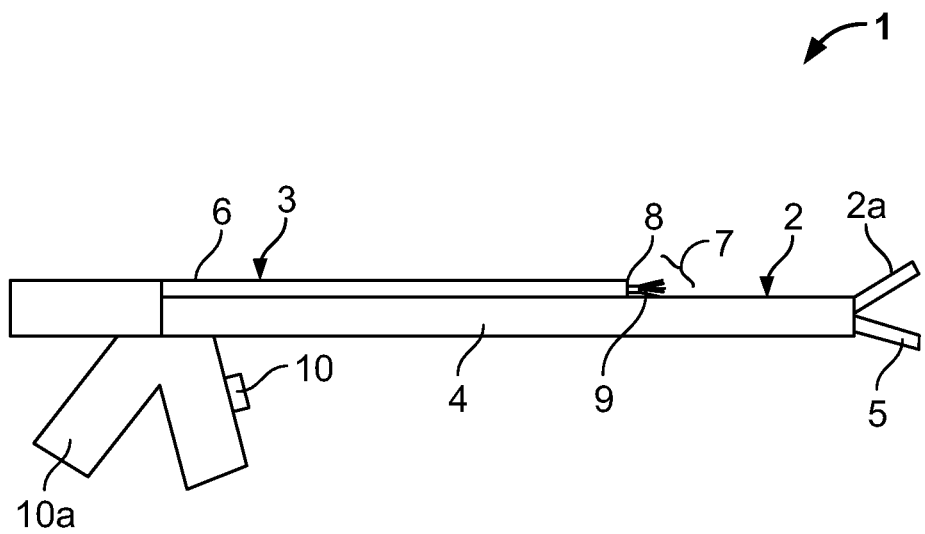
FIG. 4 is a surgical instrument according to the invention in a first configuration.

Referring firstly to FIG. 4, there is shown a surgical instrument 1 for performing a surgical procedure having an integrally arranged surgical device 2 and ion-generating electrode 3. The surgical device 2 has a conductive portion 2a and comprises an elongate body 4 with a surgical element or utensil 5, for example, a visualisation device, a tissue manipulator or modifier arranged at the distal end. The elongate body 4 comprises a shaft which is typically between 100-400 mm long and 3-12 mm in diameter, however the shaft length and diameter vary depending on the patient to be treated.

The ion-generating electrode 3 comprises a conductive arm 6 having an ion emission zone 7 at its distal end 8. The ion emission zone 7 may be formed of a sharpened or fibrous element 9, for example a brush element 9 that terminates the distal end 8 of the arm 6 and is used for projecting ions, for example electrons. This distal end 8 of the arm 6 is free so as to enable movement of the ion emission zone, however at least part of the arm 6 is attached to an outer surface of the surgical device 2, albeit directly or indirectly. At least a portion of the arm 6 is flexible, for example the flexible part of the arm 6 may be formed of memory metal. A metal such as Nitinol™ (a Nickel-Titanium alloy) can be used for higher spring loading and elasticity. Alternatively, a suitable grade of steel may be implemented, such as annealed medical grade 304V stainless steel.

The ion emission zone 7 of the ion-generating electrode 3 and the electrically conductive portion 2a of the surgical device 2 are moveable relative to each-other between a first position and a second position. Specifically, the ion emission zone 7 of the ion-generating electrode 3 is moveable relative to a side edge of the elongate body 4, whereby the ion emission zone 7 is moved from the first position to the second position along an arcuate path.

In the first position as depicted in FIG. 4, the brush element 9 is arranged in a stowed position. This enables the surgical instrument 1 to be positioned within the abdominal cavity of a patient to be treated. Once the distal end of the surgical instrument 1 is arranged intracorporealy, the brush element 9 is moveable between the first position to a second position, which is the operative position of the ion-generating electrode 3 i.e. the position in which the ion emission zone 7 of the ion-generating electrode 3 is to be activated so as to provide ions in the localised space within the patient. In the first position the distance between the ion generation zone 7 of the ion-generating electrode 3 and the conductive portion 2a of the surgical device 2 is of a value that lies outside of a pre-determined range and in the second position, the distance between the ion generation zone 7 of the ion-generating electrode 3 and the conductive portion 2a of the surgical device 2 is of a value that lies within a pre-determined range. The pre-determined range is substantially 10-50 mm and has been shown to be a separation distance that minimises a build-up of charge in the surgical instrument 1.

In an extension to this embodiment, the ion wand ion-generating electrode 3 is rotatable independent of the surgical element or utensil 5, so as to allow optimal positioning of the ion-generating electrode 3 away from the bulk tissue of patient for example by an amount up to 180° for a surgical utensil with symmetrical functionality.

An actuator 10 is arranged at a first end of an elongate body 4 of the surgical device 2 and extends from a handle portion 10a. The actuator 10 may be a trigger or an arrangement to provide a scissor mechanism. This is required for the surgeon to apply the surgical utensil 5 of the device 2 as required. The actuator 10 is also arranged to actuate the movement of the ion emission zone 7 between the first and second positions and to initiate the generation of ions from the ion emission zone 7. Therefore, the movement of the ion emission zone 7 between the first and second positions is automated based on the surgeon using the actuator 10. This is particularly desirable since the surgical instrument 1 can be configured to ensure that the ions are not generated until the second position has been obtained. In fact, the actuation of the emission of ions from the ion emission zone 7 of the ion-generating electrode 3 is prohibited when the ion emission zone 7 of the ion-generating electrode 3 is arranged in the first position.

Figure 5:
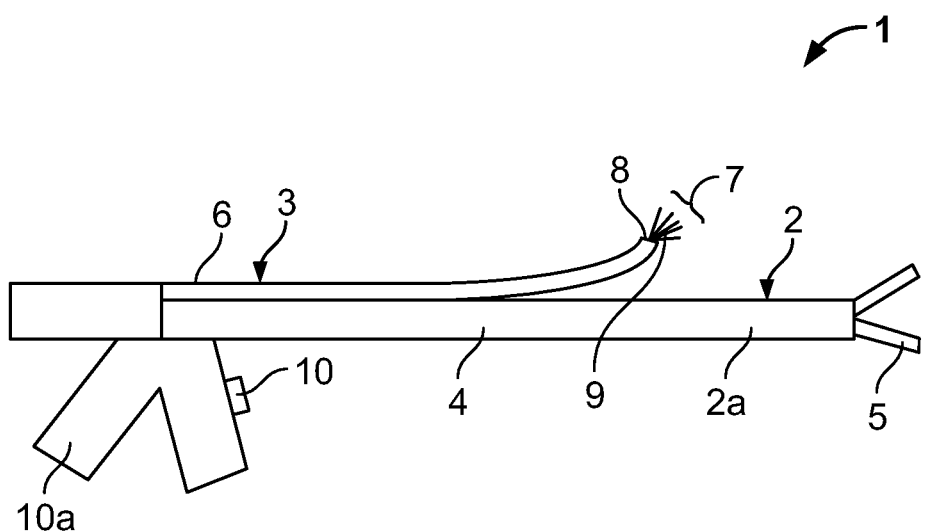
FIG. 5 is a surgical instrument in a second configuration.
Figure 6:
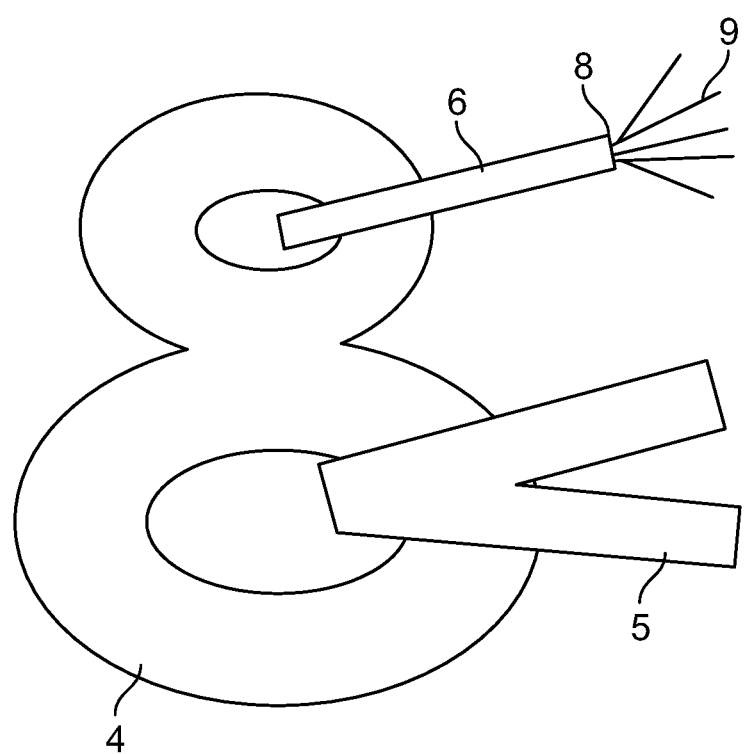
FIG. 6 is a cross section at the distal end of the integrated ion generator and surgical device.

In FIG. 5 and FIG. 6, the brush element 9 is shown in the second position which is the operative position. The second position is further dependent upon separation of the patient tissue from the ion emission zone 7 of the ion-generating electrode 3. Therefore, the brush of the ion-generating electrode must be maintained at a distance of 10-50 mm from other conductive surfaces or tissue surfaces so as to permit the surgical instrument to provide ion enhanced precipitation with minimised charge build up.

Figure 7:
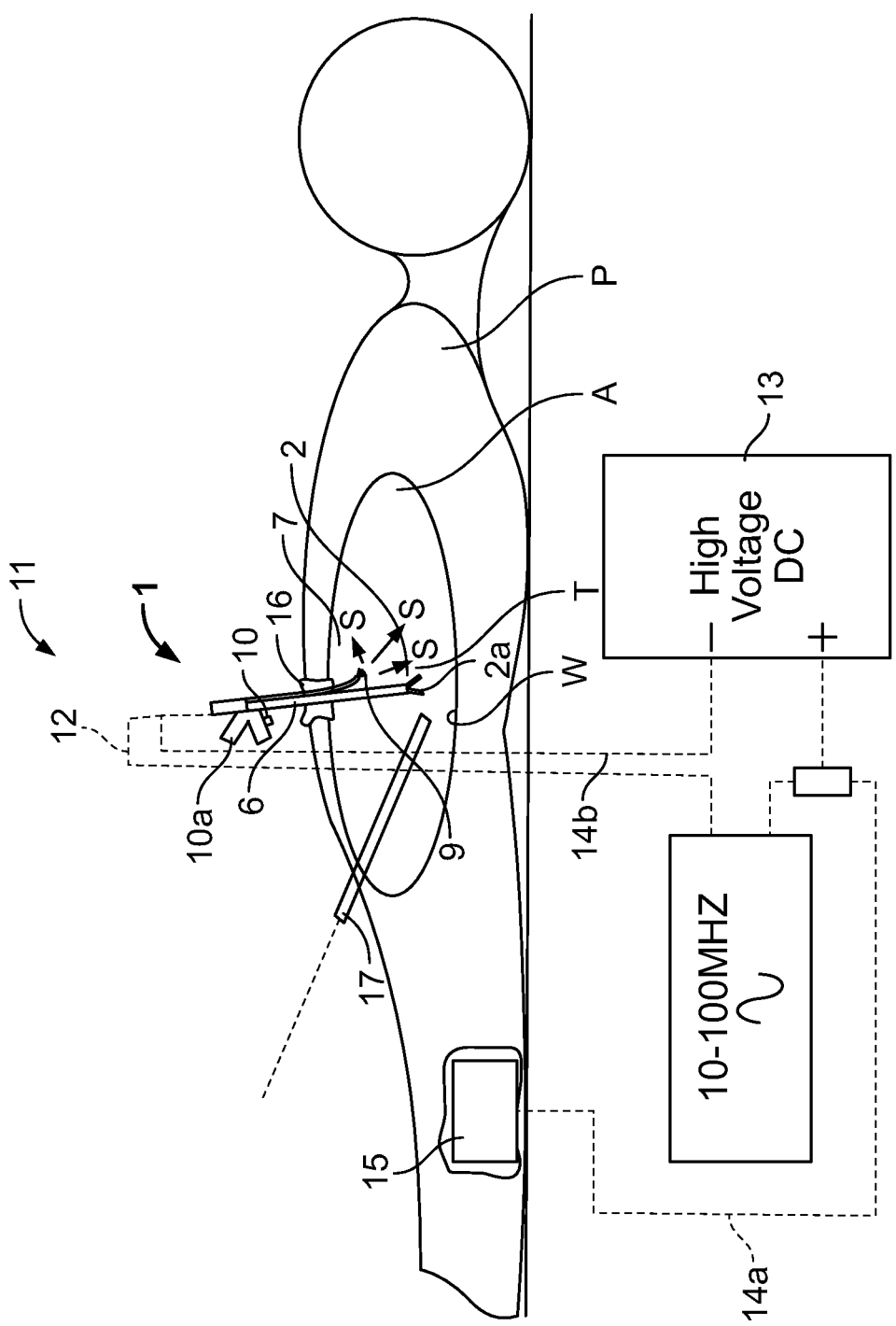
FIG. 7 is a depiction of a medical system level incorporating the integrated surgical instrument of FIG. 5, according to the invention in use on a patient.

In FIG. 7 there is shown a patient P who is undergoing a laparoscopic procedure. The surgical instrument 1 is inserted into the insufflated abdomen A via a laparoscopic access port 16 and is being used for the removal of tissue T in the abdomen A of the patient P. The surgical instrument 1 is used as part of a surgical instrument assembly 11 whereby the surgical instrument 1 is supplied with power along a power supply route 12. The surgical device 2 of the instrument 1 produces smoke particles S. The surgical instrument 1 can be operated to provide reduction or precipitation of the smoke S aerosol from the abdomen A. The surgical instrument assembly 11 includes a high voltage, but low current dc electrical source 13, conductors 14, a first ion-generating electrode 3 having an ion emission zone 7 and a second ion-generating electrode in the form of a conductive pad 15 that is attached to the patient P. At least part of the first ion-generating electrode 3 is insulated. It is shown that the first ion-generating electrode 3 comprises the conducting arm 6 and the brush element 9.

In use, the conductive pad 15 of the second ion-generating electrode is attached to the leg of the patient P, or other body part, using a conducting gel and is electrically connected to the positive pole of the high voltage source 13 by means of a conductor 14a. The conductor 14a is insulated to prevent the conductor accidentally touching against the patient. The body of the patient then becomes positively charged.

A laparoscopic telescope 17 is inserted in a separate port 19 and aimed at the distal end of the surgical apparatus. It is important not to obscure the line of site between the distal lens of the telescope and the distal end of the surgical apparatus. The retractability of the ion emission zone of the ion-generating electrode when not in use minimises the obstructive effect. The ion-generating electrode is also effective at enabling any rotational displacement possible to move the ion-generating electrode out of the line of sight when deployed.

As shown in FIGS. 5-7, the first ion-generating electrode 3 is connected to the negative pole of the high voltage source 13 via a conductor 14b. The first ion-generating electrode 3, which is integral with the surgical device 2, is then inserted into the abdomen A through a bespoke entry device 16 or a conventional laparoscopic access port. The high voltage source 13 includes a proximity detector (not shown) for sensing the ion pathway impedance between the ion emission zone 7 and the conductive portion 2a of the surgical device 2 in the first and second position. This impedance has close correlation to the physical separation between the wand and the conductive portion 2a of the surgical device 2. The high voltage source provides audible indication while the conductive portion of the wand 9 is inadequately separated from the conductive portion 2a of the device 2, as feedback to the surgeon, so allowing the surgeon to determine when adequate separation has been achieved.

Therefore, in the case the conductive portion 2a is found to be outside of a predetermined distance or range (i.e. in the first position), the ion emission zone 7 of the ion-generating electrode 3 is moved from the first position to the second position. The first position may be a stored position and the second position may be an operative position which is deemed to be an effective ion emission position.

Once the ion emission zone has been deployed into the operative position, the first ion-generating electrode 3 is negatively charged and sends a stream of electrons towards the wall W of a patient's body. The electrons attach themselves to some of the suspended atoms in the smoke particles causing the atoms to form negative ions and to become positively attracted towards the positively charged walls W of the abdomen A, where they stick thereto and are washed away at the end of the surgical procedure.

Therefore, the suspended particles in a local atmosphere produced during or after surgical procedures are reduced or precipitated by applying the above-mentioned integrated surgical instrument 1 and using a method comprising the steps, in any suitable order, of:

a) moving the ion emission zone 7 of the ion-generating electrode 3 which is integrally related to the surgical device 2 from a first position to a second position with respect to at least one conductive portion 2a of the surgical device 2;

b) commencing emission of ions from the ion emission zone 7 to thereby ionise said particles in the localised atmosphere and attract said particles towards the patient.

To initiate the method, the actuator 10 for the surgical device 2 must be actuated. On actuation of the surgical device 2 the high voltage source 13 determines the proximity of any conductive surfaces to the conductive portion 9 of the ion-generating electrode 3. If it is determined that the separation between the ion emission zone 7 and the conductive surfaces or conductive portion falls outside a predetermined range, the ion emission zone 7 of the ion-generating electrode 3 is adjusted by the surgeon from the first position to the second position, whereby the second position lies within the predetermined range considered to minimise the risk of charge build up. Ideally, the amount of deflection of the ion emission zone of the ion-generating electrode that is achieved when the actuator is operated by the surgeon is pre-set to fall inside the pre-determined range. Further, the actuator 10 actuates the ion emission zone 7 of the ion-generating electrode 3. Therefore, the actuator 10 which is used to mechanically operate the surgical device 2 also causes the deployment or movement of the ion emission zone 7 of the ion-generating electrode 3 from a first position to the second position. In the case that the device is static, e.g. a needle or a spatula tipped electrosurgical device, there is only the need for the operation of one or more electrical switches which can be mounted on the actuator 10 or can be floor mounted. However, the deployment of the ion emission zone 7 only occurs if the proximity detector of the high voltage source 13 senses that the distance between the ion emission zone 7 of the ion-generating electrode 3 and a conducting surface or portion 2a is not in conformity with the pre-determined range. This then allows the surgeon to make deflection adjustments to achieve conformity with the pre-determined range. Beneficially, this is carried out with minimal charge up of capacitances external to the high voltage dc circuit.

The actuator 10 also causes the generation or activation of the ions from the ion emission zone 7. However, the generation of the ions is only commenced subsequent to moving the ion emission zone of the ion-generating electrode 3 from the first position to the second position. Therefore, the ion activation is linked to the deployment of the ion emission zone 7 so as to minimise unwanted charge build up.

The integration of the ion-generating electrode 3 with the surgical device 2 so as to form the surgical instrument 1 requires bolstering of the relatively limited insulation barriers (not shown) so as to optimise the prevention of electrocution. Inside the elongate body 4 e.g. shaft, independent insulated lumens separate the ion-generating electrode circuit from any conductive surfaces of the surgical device. Therefore, the deployment of the ion emission zone 7 of the ion-generating electrode 3 provides sufficient functional creepage (surface insulation) distances between the ion emission zone 7 and the conducting portion 2a of the surgical device 2.

Whilst this addresses the insulation requirements under most conditions, there is still the risk of transient discharge between the ion emission zone 7 of the ion-generating electrode 3 and the conducting portion 2a of the surgical device 2. In general, the capacity to store charge depends upon the dielectric medium between the two conductive elements and their separation. The use of insulating materials in the elongate body 4 and the requirement for a compact construction, e.g. 5 mm total diameter, exacerbates the risk of significant unpleasant or hazardous electrical charge storage. Therefore, the hazard from the electrical charge build up in this capacitance requires a further risk control. Termination of one or both ends of the ion-generating electrode 3 with one or more high value resistors (not shown) (of the order of 1-100 M Ohms, and preferably 10 M Ohms) or the use of a high resistivity material to form the ion-generating electrode of similar overall resistance renders more benign the charges stored within the surgical instrument or ion-generating electrode 3, for example along their respective elongate bodies.

The hazard posed by charge build up between the surgical instrument 1 and the patient bulk tissue must also be addressed. This is achieved by incorporating a resistance of preferably 25 M Ohms between the patient return pad electric pole and at least one pole of the surgical device circuit (not shown).

For example, in the case of integration of the ion-generating electrode with a bi-polar electrosurgical accessory, neither bipolar pole is normally connected to the patient, and there are independent capacitor energy storage risks from either of the poles. Accordingly, a lower resistance selected to be insignificant electrical loading to the operation of the bipolar circuit, such as 5 M Ohms for a 300 Vrms continuous-wave bipolar circuit, is preferably placed between the two poles of the bipolar output, with a further higher e.g. 25 M Ohm resistance between one of the bipolar poles and the patient bulk potential. This assures that both bipolar poles are comparatively of a similar dc potential to each other, which is important as bipolar generators can incorporate an RF series coupling capacitor of the order of 50 nF which has a greater energy storage potential than the capacitance between the bipolar outputs together and the patient bulk tissue potential.

A further means of dealing with the increased energy storage risks arising from the greater proximity between the ion-generating electrode 3 and the conductive portions 2a of the surgical device 2 is the reduction in dc voltages achievable at the ion-generating electrode 3 relative to the patient return pad 15. It has been shown that precipitation of surgical smoke requires a minimum emitter voltage amplitude of (−)3 kV dc with improving smoke clearing rates at increasing emission voltage amplitudes. In the surgical instrument of FIGS. 5-7, the open circuit ion emission voltage is just below 10 kV dc which has been found to provide a good level of smoke clearance.

The primary current limit of 10 μA under electronic control is backed-up by the 50 μA limit that provides a total output resistance of 200 M Ohms, such that under normal fault free conditions the maximum ion emission occurs at about 8 kV dc ion emitter voltage. Therefore, in this alternative, the 10 kV dc output voltage of the upstream high voltage supply is reduced to close to 8 kV dc difference between the patient connections and the 50 µA secondary current limit is provided by independent electronic means.

Various modifications to the principles described above would suggest themselves to the skilled person. For example, the arcuate motion may instead be linear.

Whilst it has been described for the brush 9 to be deflected or deployed by moving the distal end 8 of the ion-generating electrode 3 radially, a sheath (not shown) may be retracted to release the ion emission zone 7 of the ion-generating electrode 3. Alternatively, deployment may equally be achieved by allowing the distal end of the ion-generating electrode 3 to deploy under the electrostatic attraction between the fine bristles of the brush 9 housed in similarly fine connecting insulating lumens (not shown).

Alternatively to the surgical device actuator 10 being used to actuate the deployment of the brush 9, a separate actuator (not shown), for example a slider, may be used to provide more precise manual control and a separate switch (not shown) may be applied for enabling the ion output from the ion-generating electrode.

In an alternative embodiment, multiple independently current limited tynes of the ion-generating electrode 3 may be deployed radially from the shaft 4 of the surgical device 2 and compositely limited to 10 µA. It is useful to maintain some level of current through the tynes as the point of obstruction may move. As such the system is able to dynamically move the available budget of 10 µA current to the most favorably positioned tynes. Therefore, individual tynes may be substantially switched off in response to detected proximity affecting only some of the tynes. The available 10 µA limit is then redirected to tynes which are not subject to proximity constraints. The tynes can be thought of as the ion emission zones, therefore multiple ion emission zones are provided on the ion-generating electrode which are selectively moveable dependent upon the sensed separation between the ion emission zones and the conductive portion 2a of the surgical device 2.

In a refinement of the invention, the actuator 10 may include a physical deployment scale with graduations that indicate the extent of separation between the ion emission zone of the ion-generating electrode 9 and the conductive portion 2a of the device 2. With this refinement, the surgeon is thus able to use both the audio alert and the observable scale to determine the extent of deployment and to ascertain that the circuit is able to achieve the required voltage levels needed to ionise and precipitate the locally generated smoke aerosol, with a safe level of dc current.

The powering of a surgical utensil may alternatively be achieved through foot operated switches. In such an arrangement, a switch-operated case the actuator 10 may be useful for manipulating tissue concomitantly with operation of power application switches.

Rather than the surgeon adjusting the relative distance between the by hand, it is envisaged that the process may be automated.

Placing the ion emission zone in controlled proximity with the smoke generating tip, or the visualisation device is beneficial because in the case of an electrosurgical device, significant arbitrary RF current pathways between the electrosurgical instrument shared patient return or between the surgical device inserted poles of the Electrosurgical circuit and the surroundings are prevented. The minimisation of arbitrary electrical pathways between the RF outputs and surroundings reduces the risk of RF burn or interference with contact quality circuits. Further, charge build up is minimised without affecting the precipitation or reduction of smoke and ultimately a safer and more reliable surgical technique may be performed.

The invention claimed is:

1. A surgical instrument comprising:
   a surgical device actuatable for performing a surgical procedure, the device having an electrically conductive portion,
   at least one ion-generating electrode integrally arranged with respect to the surgical device, the at least one ion-generating electrode having at least one ion emission zone for releasing a stream of electrons, and
   an actuator for actuating the surgical device for performing the surgical procedure,
   wherein the at least one ion emission zone of the at least one ion-generating electrode and the electrically conductive portion of the surgical device are moveable relative to each other between a first position and a second position, in the first position, the distance between the at least one ion emission zone of the at least one ion-generating electrode and the electrically conductive portion of the surgical device is of a value that lies outside of a pre-determined range and in the second position, the distance between the at least one ion emission zone of the at least one ion-generating electrode and the conductive portion of the surgical device is of a value that lies within a pre-determined range, the pre-determined range being a separation that maximizes an electrical smoke clearing current, the actuator being further arranged to actuate the release of the stream of electrons from the at least one ion emission zone when the at least one ion emission zone is in the second position and wherein the actuation of the release of the stream of electrons from the at least one ion emission zone is prohibited when the at least one ion emission zone is in the first position.

2. A surgical instrument according to claim 1, wherein the pre-determined range is substantially 10-50 mm.

3. A surgical instrument according to claim 1, further comprising a proximity detector for sensing the relative separation between the ion emission zone and the conductive portion of the surgical device in the first and second position.

4. A surgical instrument according to claim 3, wherein the at least one ion generating electrode comprises a plurality of ion-generating electrodes forming a plurality of ion emission zones, wherein each of the plurality of ion-generating electrodes is selectively moveable dependent upon the sensed separation between the plurality of ion emission zones and the conductive portion of the surgical device.

5. A surgical instrument according to claim 1, wherein the actuator is further arranged to enable the relative movement between the first and second positions.

6. A surgical instrument according to claim 1, wherein the second position is dependent upon the proximity of patient tissue or other conductive surface with respect to the at least one ion emission zone of the at least one ion-generating electrode.

7. A surgical instrument according to claim 1, wherein the surgical device comprises an elongate portion and the at least one ion emission zone of the at least one ion-generating electrode is moveable relative to the elongate portion.

8. A surgical instrument according to claim 1, wherein the at least one ion emission zone is moveable between the first position and the second position along an arcuate path.

9. A surgical instrument according to claim 1, wherein the at least one ion-generating electrode is formed of a sharpened or fibrous element.

10. A surgical instrument, according to claim 9, wherein the sharpened or fibrous element terminates an electrically conducting arm portion.

11. A surgical instrument according to claim 10 wherein a portion of the electrically conducting arm portion is flexible.

12. A surgical instrument according to claim 10, wherein the electrically conducting arm portion is formed of memory metal.

13. A surgical instrument according to claim 10, wherein a portion of the electrically conducting arm portion is attached to an outer surface of the surgical device.

14. A surgical instrument according to claim 1, wherein a resistive load is electrically coupled to an end of the conductive portion.

15. A surgical instrument according to claim 14, wherein the resistive value of the resistive load is in a range of 1 to 100 M Ohms.

16. A surgical instrument according to claim 1, wherein at least part of the at least one ion-generating electrode is formed of a resistive material having an effective resistance in the range of 1 to 100 M Ohms.

17. A surgical instrument assembly for removing particles suspended in a patient, the assembly comprising the surgical instrument of claim 1 and a DC voltage electrical source, the at least one ion-generating electrode of the surgical instrument is adapted to be electrically couplable with a pole of the DC voltage electrical source and the other pole of the electrical source is adapted to be electrically couplable with the patient.

18. An integrated surgical device and ion-generating electrode, the surgical device being actuatable via an actuator for performing a surgical procedure, the device having an electrically conductive portion, at least a portion of the ion-generating electrode being integrally arranged with respect to the surgical device and comprising an ion emission zone for releasing a stream of electrons, wherein the ion emission zone of the ion-generating electrode and the electrically conductive portion of the surgical device are moveable relative to each other between a first position and a second position, in the first position the distance between the ion emission zone of the ion-generating electrode and the electrically conductive portion of the surgical device is of a value that lies outside of a pre-determined range and in the second position, the distance between the ion emission zone of the ion-generating electrode and the conductive portion of the surgical device is of a value that lies within a pre-determined range, the pre-determined range being a separation that maximizes an electrical smoke clearing current the actuator being further arranged to actuate the release of the stream of electrons from the ion emission zone when the ion emission zone is in the second position and wherein the actuation of the release of the stream of electrons from the ion emission zone is prohibited when the ion emission zone is in the first position.

* * * * *